(12) United States Patent
Kominsky

(10) Patent No.: US 8,854,626 B2
(45) Date of Patent: Oct. 7, 2014

(54) ROTATING STALL DETECTION USING OPTICAL MEASUREMENT OF BLADE UNTWIST

(71) Applicant: Prime Photonics, LC, Blacksburg, VA (US)

(72) Inventor: Daniel Kominsky, Christiansburg, VA (US)

(73) Assignee: Prime Photonics, LC, Blacksburg, VA (US)

( * ) Notice: Subject to any disclaimer, the term of this patent is extended or adjusted under 35 U.S.C. 154(b) by 0 days.

(21) Appl. No.: 13/936,561

(22) Filed: Jul. 8, 2013

(65) Prior Publication Data

US 2014/0023498 A1    Jan. 23, 2014

Related U.S. Application Data

(60) Provisional application No. 61/674,062, filed on Jul. 20, 2012.

(51) Int. Cl.
| | | |
|---|---|---|
| G01N 21/55 | (2014.01) | |
| F01D 5/00 | (2006.01) | |
| F01D 17/02 | (2006.01) | |
| F01D 21/00 | (2006.01) | |

(52) U.S. Cl.
CPC .............. *F01D 5/00* (2013.01); *G01N 21/553* (2013.01); *G01N 21/554* (2013.01); *F01D 17/02* (2013.01); *F01D 21/003* (2013.01); *F05D 2260/80* (2013.01); *F05D 2270/101* (2013.01); *F05D 2270/804* (2013.01)
USPC ........................................................ 356/445

(58) Field of Classification Search
CPC .......... G08C 17/02; B64D 43/02; F02C 7/26; F02C 9/16; F02C 9/20; F02C 9/28; F02D 17/04; F02D 2200/1002; F02D 2200/1004; F02D 29/02; F02D 41/1497; F02D 41/22; F04B 17/05; F04B 25/00; F04B 49/00
See application file for complete search history.

(56) References Cited

U.S. PATENT DOCUMENTS

| | | | |
|---|---|---|---|
| 4,049,644 A | | 9/1977 | Wennerstrom |
| 4,060,329 A | * | 11/1977 | Ellis ............................ 356/614 |

(Continued)

OTHER PUBLICATIONS

Cousins, William T., The Dynamics of Stall and Surge Behavior in Axial-Centrifugal Compressors, Dissertation submitted to Virginia Tech for Ph.D. in Mechanical Engineering, Dec. 2, 1997.

(Continued)

*Primary Examiner* — Michael P Stafira
(74) *Attorney, Agent, or Firm* — New River Valley IP Law, PC; Michele L. Mayberry

(57) ABSTRACT

Systems and methods are provided for real-time detection of the onset of stall in turbomachinery, such as compressor stall. The methods are capable of detecting and analyzing time of arrival of the chord of the blade at a sensor array to provide an indication of the onset of compressor stall. Systems for detecting the onset of compressor stall include: light sources; a plurality of linearly arranged optical fibers for transmitting light from the light sources and for receiving transmitted light reflected from a blade; a detector for measuring intensity of the reflected light; and a processor for analyzing the intensity of the reflected light to determine blade twist angle and from the blade twist angle identify onset of compressor stall. The invention can prevent the needless loss of life and assets caused by compressor stall that may lead to unexpected catastrophic failure of an engine.

19 Claims, 11 Drawing Sheets

(56) References Cited

U.S. PATENT DOCUMENTS

| | | |
|---|---|---|
| 5,051,918 A | 9/1991 | Parsons |
| 5,463,458 A * | 10/1995 | Berkcan .......... 356/28 |
| 6,253,126 B1 * | 6/2001 | Palmer ............ 701/14 |
| 6,474,935 B1 | 11/2002 | Crotty et al. |
| 6,857,845 B2 | 2/2005 | Stabley et al. |
| 7,344,360 B2 | 3/2008 | Wetzel |
| 7,409,854 B2 * | 8/2008 | Teolis et al. ......... 73/114.04 |
| 7,424,823 B2 | 9/2008 | Teolis et al. |
| 7,783,395 B2 | 8/2010 | Melville |
| 7,836,772 B2 | 11/2010 | Twerdochlib |
| 7,905,702 B2 | 3/2011 | Stabley et al. |
| 7,938,623 B2 | 5/2011 | Cairo |
| 8,164,761 B2 | 4/2012 | Kominsky |
| 2004/0037693 A1 | 2/2004 | Stabley et al. |
| 2006/0120197 A1 * | 6/2006 | Teolis et al. ............ 365/226 |
| 2006/0122798 A1 | 6/2006 | Teolis et al. |
| 2010/0114502 A1 | 5/2010 | Badami et al. |
| 2010/0177299 A1 | 7/2010 | Kominsky |
| 2013/0314694 A1 * | 11/2013 | Tchoryk et al. ......... 356/28.5 |

OTHER PUBLICATIONS

Mehmed, Oral; Janetzke, David C., Fan Blade Deflection Measurement and Analyses Correlation, NASA, Glenn Research Center, Mar. 1997, Document ID 20050179332.

* cited by examiner

ROTATING STALL DETECTION USING OPTICAL MEASUREMENT OF BLADE UNTWIST

CROSS REFERENCE TO RELATED APPLICATIONS

This application claims priority to and the benefit of the filing date of U.S. Provisional Application No. 61/674,062, filed Jul. 20, 2012, the disclosure of which is hereby incorporated by reference herein in its entirety.

BACKGROUND OF THE INVENTION

1. Field of the Invention

Embodiments of the present invention relate to methods, systems and devices for detecting rotating stall in turbomachinery. A system is provided for detecting the onset of compressor stall, which comprises a line probe for transmitting light toward and receiving reflected light from the surface of a blade moving through the optical path of the line probe and a detector for measuring the intensity of the reflected light to determine a change in blade angle indicative of blade stall. Embodiments of the invention are capable of identifying in real time the onset of compressor stall in both axial and centrifugal flow compressors.

2. Description of Related Art

Rotating stall within a compressor is known to be a factor which can lead to the occurrence of compressor surge. In a normally operating compressor, the air flows predominantly along the axis of the compressor. In the event of rotating stall, a portion of air begins a behavior in which it substantially propagates around the compressor stage with the blades. In this case a small proportion of compressor blades experience flow separation, creating a region of stalled air which circulates around the engine at roughly half the speed of the rotor's revolution. Some key impacts of rotating stall include reduction in engine output power, and excess mechanical loading on the compressor blades. Once compressor stall is initiated, it can spread sequentially to other blades, eventually resulting in the stalling of the majority of the rotor, and leading to surge.

Rotating stall can progress to initiate axi-symmetric stall. In an axi-symmetric stall, the entire compressor stage loses the ability to operate, resulting in a local reversal of the air flow. This in turn can cause the stalling of the preceding stage, and allow the phenomenon to propagate forwards through the engine, resulting in compressor surge. In this case the engine completely loses compression, resulting in a reversal of flow through the engine. This in turn, can cause engine wear, extreme vibration, and even total destruction of the engine. Often the conditions which create the surge remain in place for a period of several seconds, resulting in a repeated surging of the engine.

Compressor surge is a major concern of both the US military and civilian aircraft industries. The phenomenon has been identified as the cause of several incidents that have resulted in the death and injury to passengers, pilots, and staff. Operating the turbine engine so as to avoid compressor stall also leads to a loss in efficiency of the turbine engine, particularly at higher speeds.

There are numerous causes of compressor stall and surge, ranging from attempting to increase the engine speed too rapidly, to ingestion of a foreign object, erosion of engine parts, or extreme maneuvering. Surge can also be caused by an engine ingesting hot gases, during thrust reversal for example. Currently, in order to prevent compressor stall and surge, engines must be operated at sub optimal efficiency, particularly at higher speeds.

By detecting rotating stall, remediation actions may be undertaken to suppress the rotating stall prior to the occurrence of surge. Methods are known for suppressing rotating stall using active controls. One method for performing this suppression is through the injection of high pressure air at specific locations and times. This requires early knowledge of the rotating stall before it spreads to create the surge. Previous work has been performed on trying to detect surge precursors in compressors, such as using high speed pressure measurements as described in the dissertation of Dr. William Cousins, Virginia Tech, 1997. This research indicates that the amount of time required for a rotating stall to evolve into a compressor surge is dependent on the current speed of the compressor, which generally takes at least a couple of revolutions, and at lower speeds, the time increases further.

A known approach for detecting the onset of compressor stall is disclosed in U.S. Pat. No. 6,474,935 entitled "Optical Stall Precursor Sensor Apparatus and Method for Application on Axial Flow Compressors." This approach measures the time of arrival of the tip of an airfoil and compares this data with a predetermined fixed value. If the measurement is greater than the reference, the system concludes a stall condition is present. Time of arrival of the blade tip, however, can be dependent on many factors and is not necessarily an accurate indicator of compressor stall. For example, the time of arrival of a blade tip can be altered when a blade is damaged by a domestic or foreign object. As a result, there may be a defect in the blade tip that alters its time of arrival but that does not contribute to compressor surge. If the change in time of arrival is above the fixed threshold, then a false indicator of surge will result. A more accurate time of arrival based measurement would take into account a plurality of data points on the blade surface rather than just the blade tip. Further, comparing the change in time of arrival of a blade tip to only a fixed pre-determined reference may not take into account changing conditions of the rotor during operation. Time of arrival of the blade tip may change during operation as a natural result of the operating conditions. If the pre-determined reference value is not updated to reflect the new operating conditions, then again a false indication of compressor stall may result.

Other approaches like those described in U.S. Pat. Nos. 7,783,395 and 7,905,702 use sensors to identify a stall condition by detecting a change in pressure flow resulting from stalled air circulating around the rotor instead of through the rotor. Such approaches detect stall when it has already occurred because the decrease in pressure flow only occurs as a result of stall. These systems therefore are unable to provide a control signal to initiate procedures to prevent the stall from occurring.

What is lacking is an early warning sensor capable of accurately detecting and preventing a stall condition prior to compressor surge. A reliable system is needed that monitors multiple points on a blade and compares the position of those points with reference values obtained from other blades, where the reference values are updated to account for changing conditions of the compressor during operation.

SUMMARY OF THE INVENTION

Embodiments of the present invention relate to the development and implementation of a real time, uncooled, high temperature early detection mechanism for compressor stall as a key enabler in the prevention of major engine mishaps, and ultimately in the increase of engine performance.

One principle of the invention is the ability to detect a change in the twist profile of a blade by comparing the twist profile of one blade to that of previous twist profiles of the same blade or other blades. Making this comparison with data obtained during the same or previous revolutions of the rotor instead of with a fixed pre-determined value is a more accurate way of identifying a blade stall and thus predicting the onset of compressor stall.

More particularly, the change in twist angle of a blade can be measured using a sensing plane provided by a plurality of optical fibers in a line probe. The profile of light reflected from a blade subject to the optical path of a line probe will change as a blade is untwisted from a loaded condition. An unloaded blade is a good indicator of the potential onset of compressor stall Thus, identifying stall, or an unloaded blade condition, of one or more blades would be a good predictor of imminent compressor stall. The twist profile of a loaded blade as compared with an unloaded blade is different. One difference is that the spacing between two receive signals of a loaded blade will be greater than the spacing between the same receive signals of an unloaded blade. As the spacing between receive signals within the twist profile is shortened, untwist of the blade (caused by unloading) occurs and when unloaded this indicates stall of that blade and the potential for subsequent compressor stall.

An object of the present invention provides a fiber-optic based rotating stall detection system (RSDS) as shown in FIG. 1, which system comprises a plurality of optical fibers, a light source in operable communication with one or more of the optical fibers, a detector in operable communication with one or more of the plurality of optical fibers, and software for processing data obtained from the detector for determining blade angle.

Specifically, an object of the present invention includes one or more light source (also referred to as an optical source) and a plurality of optical fibers arranged to provide a line probe operably configured for transmitting light from the light source(s), receiving light reflected from one or more blades passing through the transmitted light, and determining the intensity of the reflected light. Optionally, the light transmitted and/or reflected can pass through a lens for providing more or less focused light for a particular application. Further, a hermetic window can be used to protect the optical components from the blades or other parts of the compressor.

Rotating stall detection systems of the invention can incorporate the capabilities of any type of sensor technology. Sensors used in preferred embodiments are optical sensors. For example, the technology disclosed in U.S. Pat. No. 8,164,761 issued Apr. 24, 2012 and entitled "Differential Focus Blade Clearance Probe and Methods for Using Same," and disclosed in US Published Application No. 2010/0177299, entitled "Differential Focus Blade Clearance Probe," published Jul. 15, 2010, would provide a sufficient platform for obtaining the needed data for determining stall onset according to methods of the invention. Such sensors are capable of providing real time measurements of blade tip clearance, time of arrival, blade speed, detection of high cycle fatigue including blade motion, and detection of foreign object damage (FOD) at uncooled temperatures of up to 510° C. (950° F.).

In preferred embodiments, the sensors are used to collect data for making blade angle determinations of one or more blades of a compressor. A representative compressor is shown in the schematic of FIG. 2. The blade angle measurements can then be used to predict the onset of compressor stall and/or the one or more stalled blade.

Methods of determining blade angle for predicting the onset of compressor stall are also included within the scope of the invention. For example, a method of detecting compressor stall according to the invention can comprise transmitting light from one or more and preferably a plurality of optical fibers arranged linearly relative to one another toward a moving blade of a compressor, receiving light reflected from the blade into a plurality of optical fibers and into an optical detector to measure the reflected light intensity, determining blade angle from the reflected light data, and determining whether one or more blades is stalled or whether the stall is imminent.

An object of the present invention provides a system for detecting the onset of compressor stall comprising: one or more light source; a plurality of optical fibers linearly arranged in a row for transmitting light from the light source and for receiving transmitted light reflected from a blade; a detector for measuring intensity of the reflected light; and a processor in operable communication with the detector for measuring the intensity of the reflected light to determine blade angle and identify onset of compressor stall.

Another object of the present invention is a computer program embodied in a computer-readable storage medium, which when executed, enables a computer to perform a method for detecting the onset of compressor stall, the method comprising: transmitting a plane of light from one or more and preferably an array of two or more optical fibers toward one or more blades of a compressor moving through the plane of light; receiving light reflected from the blade into a plurality of optical fibers which are arranged in a row; measuring intensity of light reflected from the blade; calculating blade twist angle from the light intensity; and comparing the blade twist angle to a twist angle of one or more preceding blade to determine onset of compressor stall.

A computer program according to an embodiment of the invention can further comprise signaling a control system in operable communication with the compressor to initiate stall avoidance procedures.

A further object of the invention is a method for detecting the onset of compressor stall comprising: transmitting a plane of light from one or more and preferably an array of two or more optical fibers toward one or more blades of a compressor moving through the plane of light; receiving light reflected from the blade(s) into a plurality of optical fibers arranged in a row; measuring intensity of light reflected from the blade; calculating blade twist angle from the light intensity; and comparing the blade twist angle to a twist angle of one or more preceding blade to determine the onset of compressor stall. Such methods can further comprise the step of signaling a control system in operable communication with the compressor to initiate stall avoidance procedures.

BRIEF DESCRIPTION OF THE DRAWINGS

The accompanying drawings illustrate certain aspects of some embodiments of the present invention, and should not be used to limit or define the invention. Together with the written description the drawings serve to explain certain principles of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Figure 1:
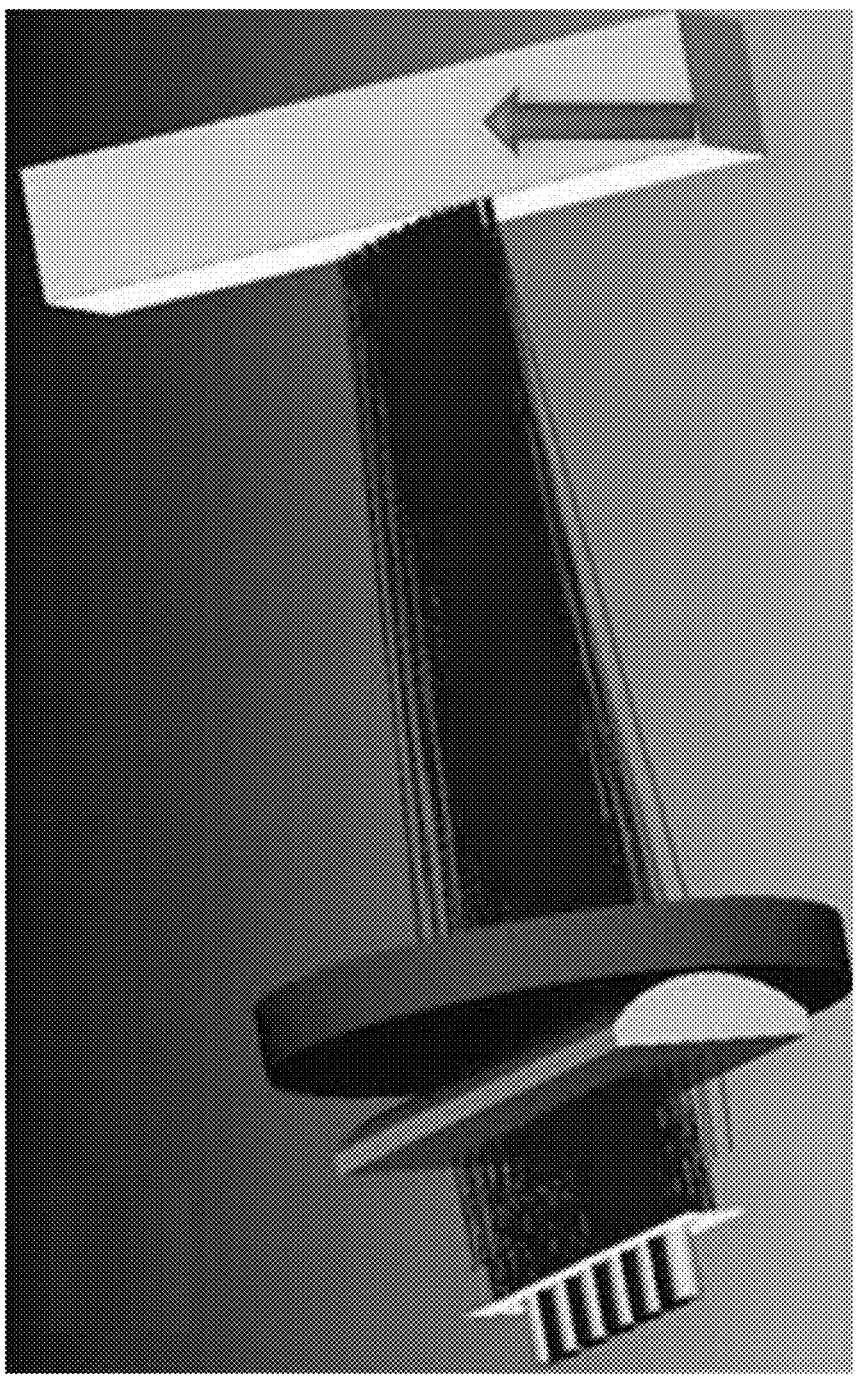
FIG. 1 is a schematic diagram illustrating an embodiment of a fiber-optic based rotating stall detection system (RSDS) according to the invention.

A representative system of the invention is shown in FIG. 1. Provided in FIG. 1 is a schematic diagram illustrating an embodiment of a fiber-optic based rotating stall detection system (RSDS). The system generally comprises a line of optical fibers behind a cylindrical lens, optionally shielded from the engine environment by a hermetic window, where every other fiber either transmits light toward or receives reflected light from a blade moving through the optical path of the probe. In embodiments of the methods, systems, and devices of the invention, the line probe can comprise a row of optical fibers, wherein one or more fiber is used to transmit light toward the blade and the remaining optical fibers of the plurality are used to receive light reflected from the blade, The operational end of the probe begins at the left side of FIG. 1 with a series of interleaved transmit and receive fibers lineraly arranged and aligned in a row. In this manner, the light from the optical fibers is transmitted toward a blade of a compressor in a generally planar beam, such that when the beam intersects the blade the light appears as a line on the blade. In front of the row of fibers is an optional high temperature cylindrical lens (e.g., made of either silica or sapphire, depending on the temperature of application). The cylindrical lens focuses the launched light into a horizontal stripe which the blade passes through. The array of receive fibers each samples a portion of the illuminated stripe that is reflected from the blade. Since embodiments of probe systems of the present invention are generally built into the surface surrounding the rotor within the compressor, it is preferred that all of these components usually sit behind a hermetic window of single crystal sapphire as shown.

Figure 2:
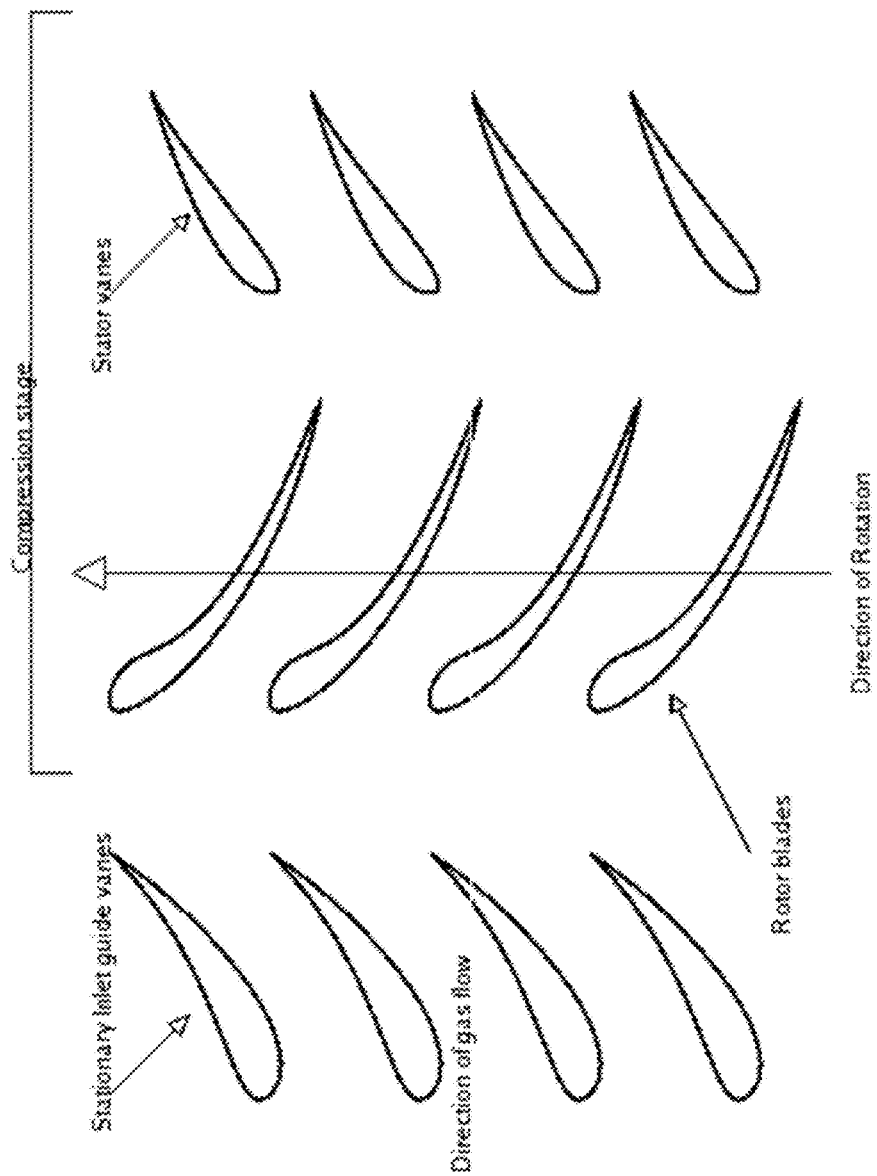
FIG. 2 is a schematic diagram of a compressor map showing the direction of motion of the compressor blades relative to the rest of the compressor.

FIG. 2 shows the layout of a typical axial flow compressor. Ideally, all of the gas flows into the left side of the diagram, through the center column of blades, and out of the right side of the diagram. During this normal operation of the compressor, the rotor blades receive more resistance because the blades are pushing the gas through the compressor. As such, they have a greater load, and consequently, a larger twist angle relative to the axis of rotation. When compressor stall occurs, some of the gas begins to flow in the direction of rotation of the rotor blades, instead of through the rotor blades, which decreases the load on the blades and decreases the twist angle relative to the axis of rotation.

Figure 3:
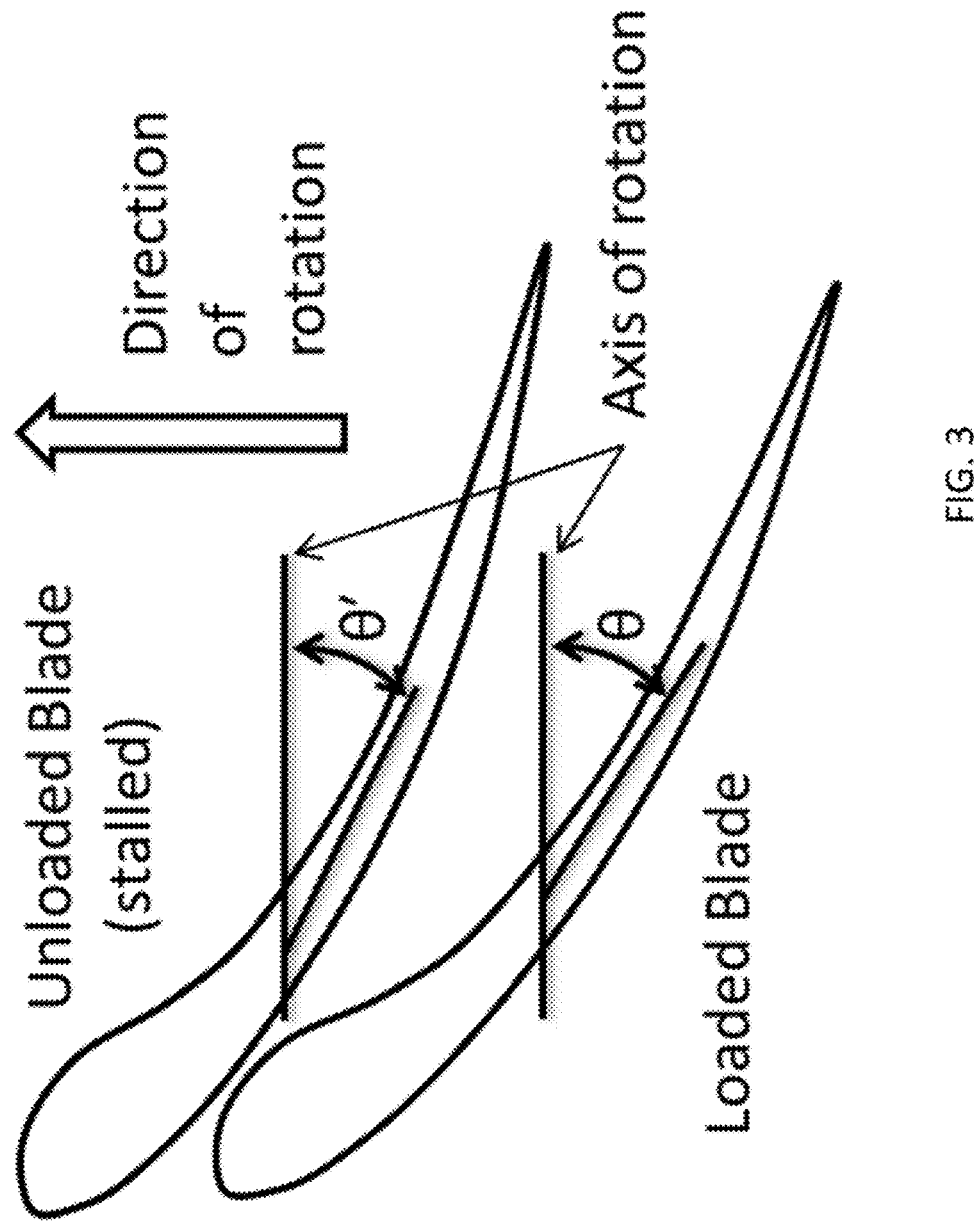
FIG. 3 is a schematic diagram of an end of a compressor blade under both the loaded condition (normal operation) and the unloaded condition (stalled), illustrating the different angles of the blades relative to the axis of rotation in the two conditions.

The Rotating Stall Detection System (RSDS) of embodiments of the invention operates by measuring the change in blade untwist which occurs as compressor stall results in reduction of the aerodynamic loading. Very generally, this principle of operation is illustrated in FIG. 3. As a compressor blade operates, the aerodynamic loading causes the rotor blades to twist under the load (shown as the loaded blade in the lower portion of FIG. 3). When a blade stalls, a pocket of air begins traveling with the blade around the circumference of the engine (usually at 50-70% of the blade's speed). As a result, the air exerts far less force on the blade, allowing the blade to untwist, i.e., the blade reverts partially to its unloaded twist profile (shown as unloaded blade in the upper portion of FIG. 3).

Figure 4A:
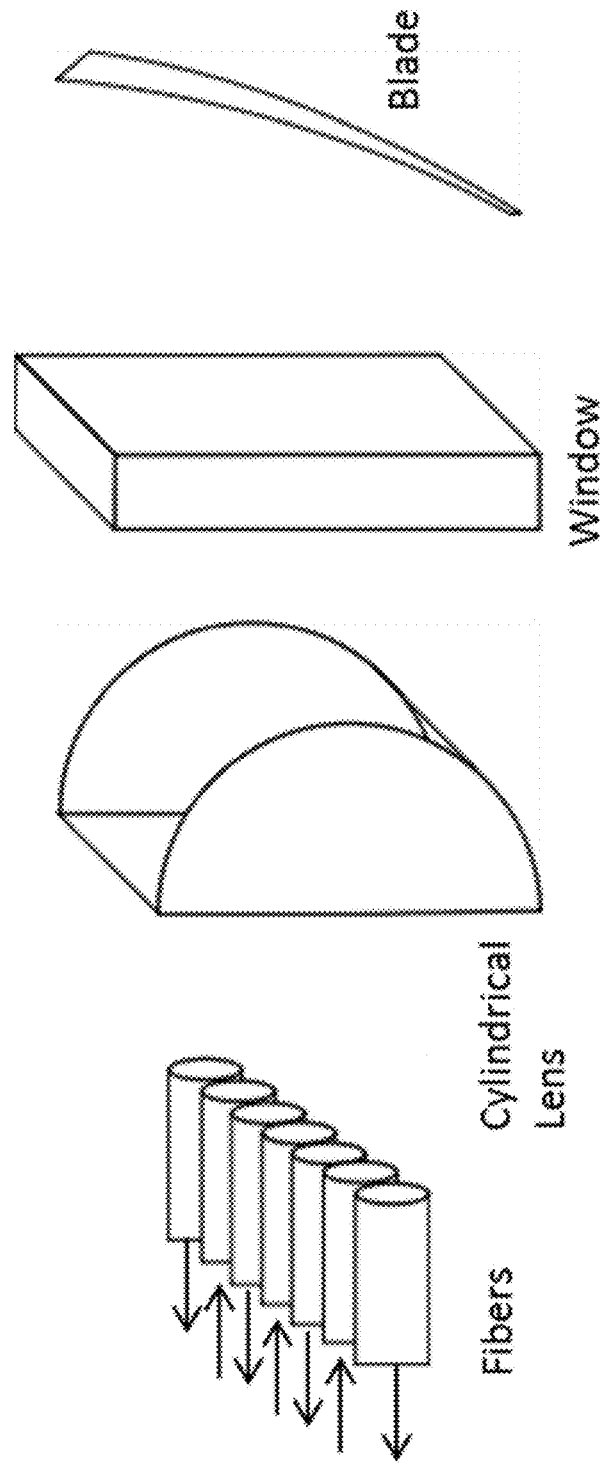
FIG. 4A is a schematic diagram showing a perspective view of an embodiment of a system of the invention, which comprises a series of light sources and detectors on the left side of the figure which are aligned in a row behind a cylindrical lens.
Figure 4B:
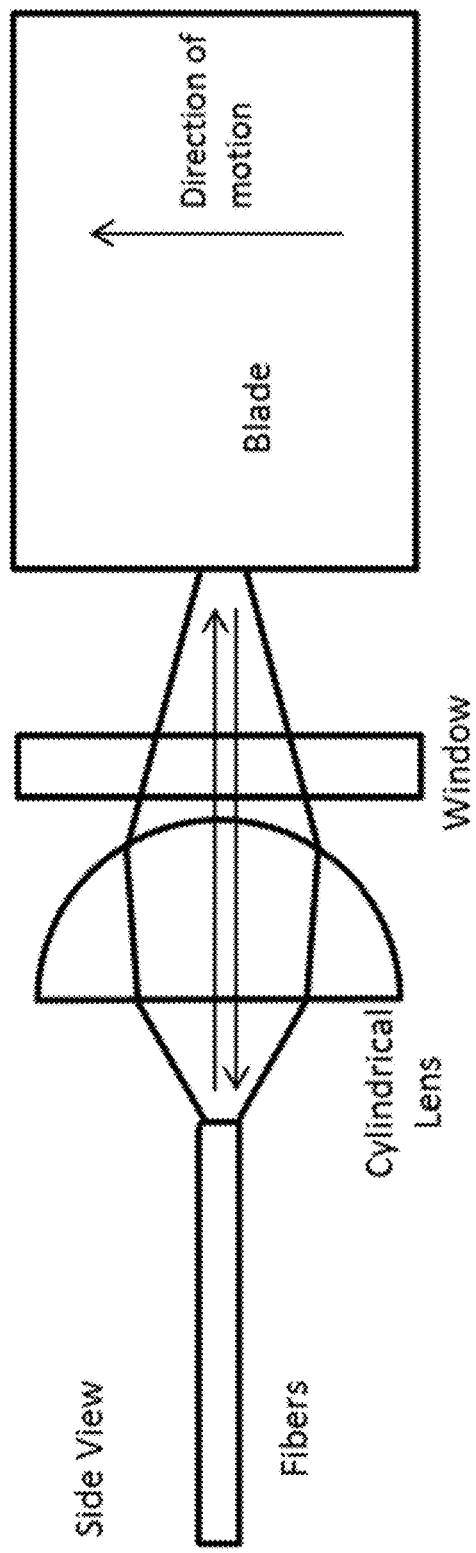
FIG. 4B is a schematic diagram showing a side view of the system of FIG. 4A, illustrating the optical path of the beams of light going from the fibers, reflecting from the end of the blade, and returning to the fibers.
Figure 4C:
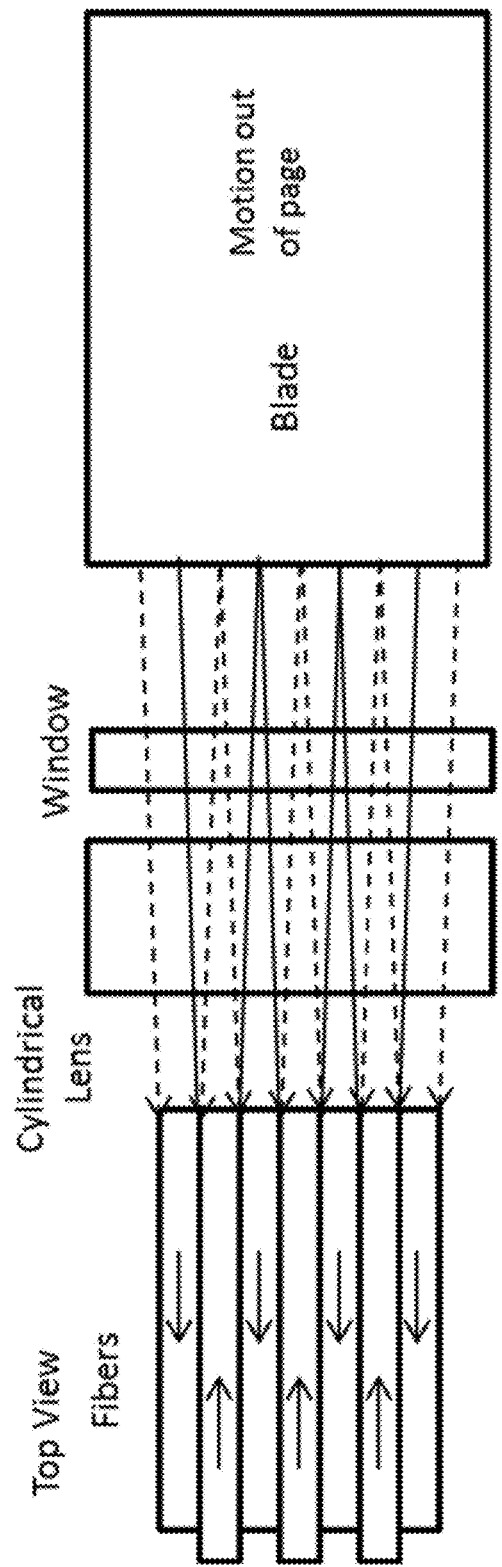
FIG. 4C is a schematic diagram showing a top view of the system of FIG. 4A, illustrating the outgoing beams of light and the returning beams of light, which shows the individual detectors being responsive to different portions of the blade.

Various components that can be included in the sensor array of preferred embodiments of the invention are shown in FIGS. 4A-C. A perspective view of such a system is shown in FIG. 4A, which provides a system with a light source, a detector, and a plurality of optical fibers for transmitting light from the light source and for delivering light reflected from one or more blades back to the detector. In this embodiment, the optical fibers are arranged linearly as a line probe. Three optical fibers are used to transmit light from the light source to one or more blades passing by the line probe. Four optical fibers are used for collecting transmitted light as it is reflected off of the surface of the blade passing through the light path. Any number of transmitting (output) optical fibers and any number of receiving (input) optical fibers can be used. In preferred embodiments, a line probe comprising ten optical fibers is used, with five output fibers and five receive fibers. Also shown in FIG. 4A are optional components such as a lens and hermetic window.

In embodiments, and as further shown in FIGS. 4A-C, the optical fibers are arranged in an alternating pattern for transmitting and receiving the light. It is not critical which fibers of the line probe are transmit fibers and which are receive fibers. For example, and in preferred embodiments, every other fiber can be a fiber for transmitting the light. As shown in FIG. 4B, a cylindrical lens can be used for converging the several beams of light transmitted from the light source(s) into a more condensed light beam. The hermetic window can be made of a material, such as single crystal sapphire, having insulator properties in order to shield the sensor array from the high temperature environment typical of operating compressors. The window is then hermetically sealed to further insulate and protect the probe from the temperate and weather-variable environment of the compressor where the rotor is located.

Optical signals are transmitted and reflected in a pattern as shown in FIG. 4C. The solid lines indicate the pattern by which the optical signals are focused through the cylindrical lens into a more concentrated light beam through which a blade will pass. The dotted lines represent how the light beam is reflected from the surface of the blade and sent back through receive optical fibers to a detector. Optionally, the system can use a detector without receive optical fibers, or a switch or splitter can be activated to receive the reflected light through the same optical fibers that initially transmitted the light. For example, systems of the invention can comprise one or more optical sources and/or one or more optical detectors incorporated into the probe, with or without one or more optical fibers for transmitting light from the optical source(s) or to the optical detector(s).

Figure 5:
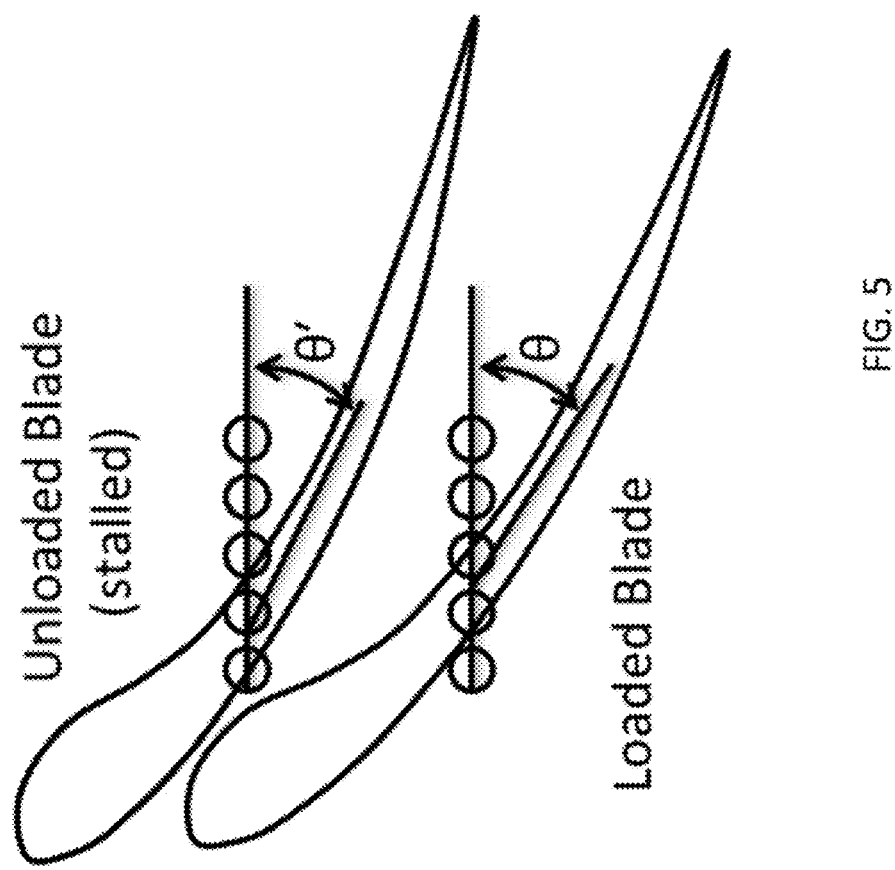
FIG. 5 is a schematic drawing showing untwist of an axial compressor blade when experiencing rotating stall, where the five circles show receive zones of the fibers in the probe.

FIG. 5 demonstrates one principle of operation of the RSDS system. The system comprises sensors that detect the blade's time of arrival at a series of locations along the chord of the blade (shown as the rows of dots). The rows of dots represent the light beam being transmitted toward and/or reflected from the surface of the blade. The sensor array, represented by the circles, is oriented along the axis of rotation of the blade. The RSDS detects the angle of the blade tip by measuring the relative time at which the reflection is observed by each fiber. Because the rotor speed does not change as compressor stall begins to occur, the blades will continue to cross the axis of rotation at the same interval of time. However, the stall begins to change the twist angle relative to this axis and so the time of arrival as well as the total time duration for the blade to cross an individual sensor region will vary slightly.

Figure 6:
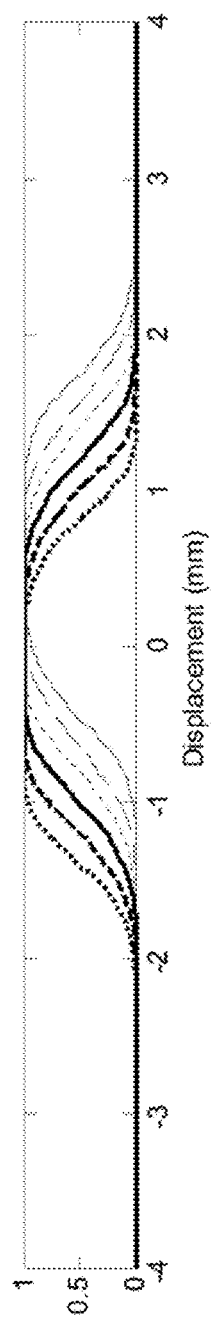
FIG. 6 is a graph showing the optical response of the individual receive fibers of the RSDS probe for a given blade angle, as the blade passes in front of the probe.
Figure 7:
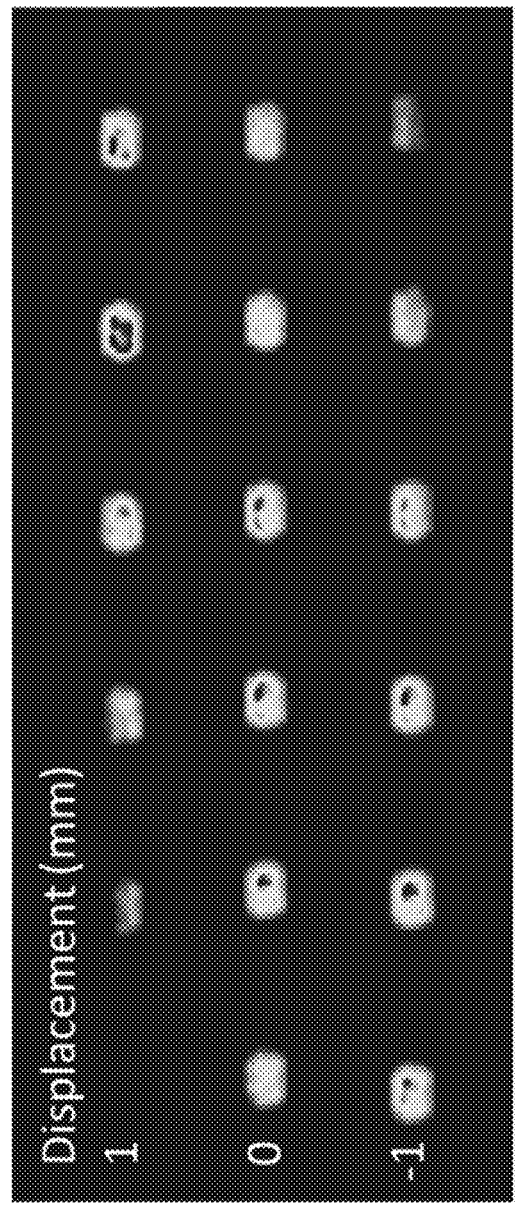
FIG. 7 is a graphical simulation of the progression of illumination of each receive fiber in the probe as a blade passes (with fixed angle).

Because the blade is angled relative to the measurement sites, a sequential rippling in the response of each detection point as the blade passes the sensing plane is observed (FIGS. 6 and 7). More particularly, FIG. 6 is a graph showing the optical response of the individual receive fibers of the RSDS probe for a given blade angle, as the blade passes in front of the probe. Each pattern of line indicates the response of a single channel of the probe. FIG. 7 is a graphical simulation of the progression of illumination of each receive fiber in the probe as a blade passes (with fixed angle).

An increase in the magnitude of the blade angle relative to the axis of rotation (which indicates the blade is in a loaded condition) is detectable by an increasing separation of the response from each channel compared to the width of the pulse. Likewise, as the blade is unloaded due to stall conditions, the magnitude of the angle of the blade relative to the measurement plane is reduced, and the puke responses from each of the individual optical channels move closer together. Blade tip speed is compensated by measuring the pulse separation as a fraction of pulse width.

Figure 8:
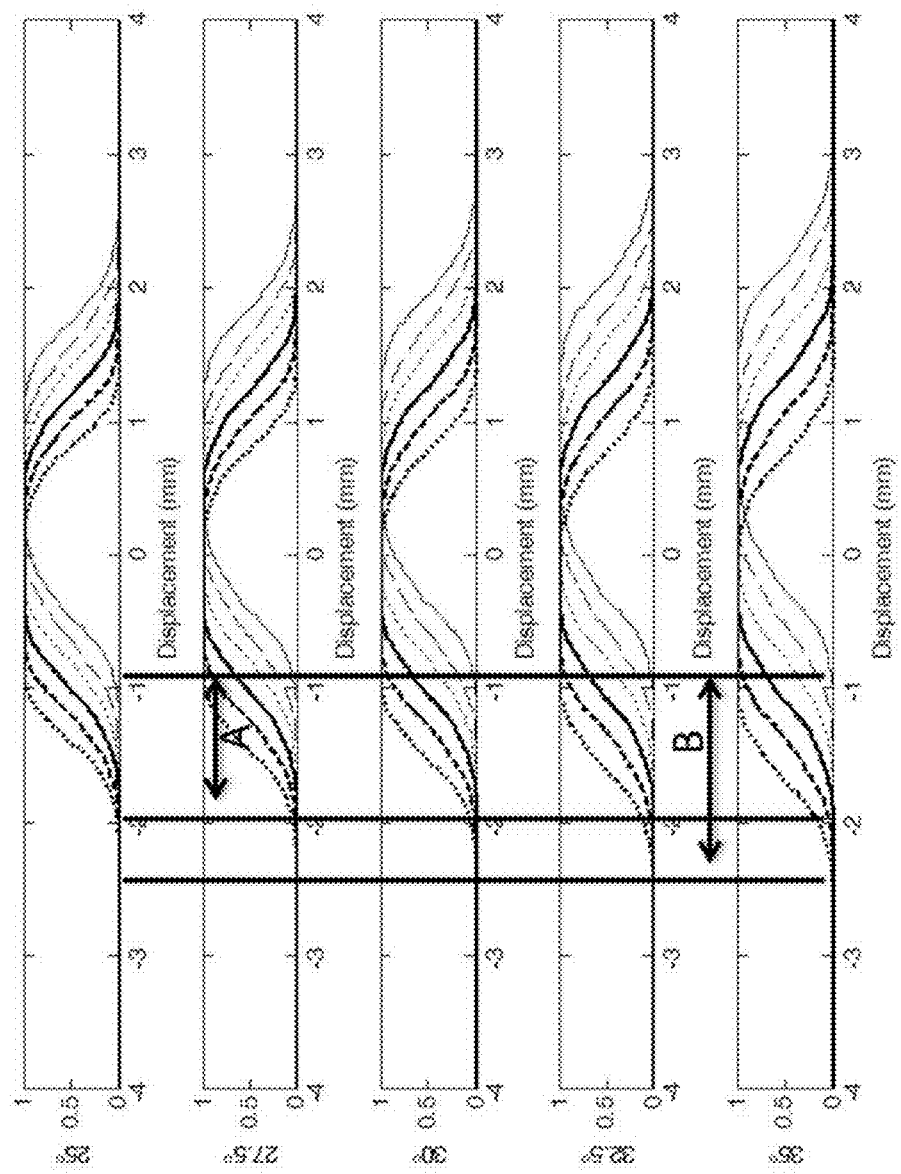
FIG. 8 is a graph showing simulation results demonstrating the change in signal timing with increasing angle of the rotor blade.

FIG. 8 shows one embodiment of how the blade angle measurement can be detected in practice. In this embodiment, a line probe is used which comprises a plurality of output and receive fibers. More particularly, five output fibers are used to transmit light toward a blade or blades of a compressor. The light is reflected from the blade(s) and received through six receive fibers and detected by a detector. According to other embodiments, any number of output or receive fibers can be used and in any configuration. Here, the output fibers are alternated every other fiber with the input fibers.

Each of the plots of FIG. 8 shows the intensity of the light detected by each of the gray receive fibers of the set up shown in FIG. 1. The bolded dotted line, • • •, of FIG. 8 corresponds with the left-most receive fiber shown in FIG. 1. Moving rightward through the line probe to sequential fibers, the bolded dashed line, - - -, of FIG. 8 corresponds with the second receive fiber, while the bolded solid line corresponds with the third receive fiber, the unbolded dotted line, • • •, corresponds with the fourth receive fiber, the unbolded dashed line, - - -, corresponds with the fifth receive fiber, and the unbolded solid line corresponds with the sixth or right-most receive fiber of the line probe.

The top plot of FIG. 8 shows the response on each of the fibers for a blade passing with an angle relative to the line probe of 25° (θ in FIG. 5). In particular, the blade angle is measured relative to a plane parallel to or in which light from the line probe is disposed. It is not necessary that the blade angle be measured relative only to the line probe and it is possible to measure blade angle relative to any other fixed reference as well. Proceeding down through the charts of FIG. 8, the blade is rotated in successive steps of 2.5° to a maximum of 35° in the bottom chart. Arrow A, in the top chart indicates the amount of time between the start of the response on the first fiber (bolded dotted line) and the start of the response on the last fiber (unbolded solid line) for the case of 25°. Arrow B, in the bottom plot, shows the equivalent time period for the case of 35°. This difference in the timing feature is a direct measure of the blade angle, and hence the amount of aerodynamic loading on the blade. This agrees with physical logic, since with increased blade angle, the rotor must rotate further in its revolution to bring the trailing edge of the blade up to the same plane.

The output of the sensor system is illustrated in FIG. 8 which shows a collection of example simulation results demonstrating the change in signal timing with increasing angle of the rotor blade. With the rotor blade normal to the direction of travel (25°—top graph), all fibers show the same time series distribution. Arrow A marks the delay between the start of the yellow signal and the blue signal for the 25° case. As the angle of attack increases progressively up to 35° we see steadily increasing separation of the time responses of the individual fibers. Arrow B shows the equivalent delay between the two fiber's responses for the 35° blade angle. The large variations in blade angle are used to accentuate the effect, rather than as a representative set of values.

Figure 9:
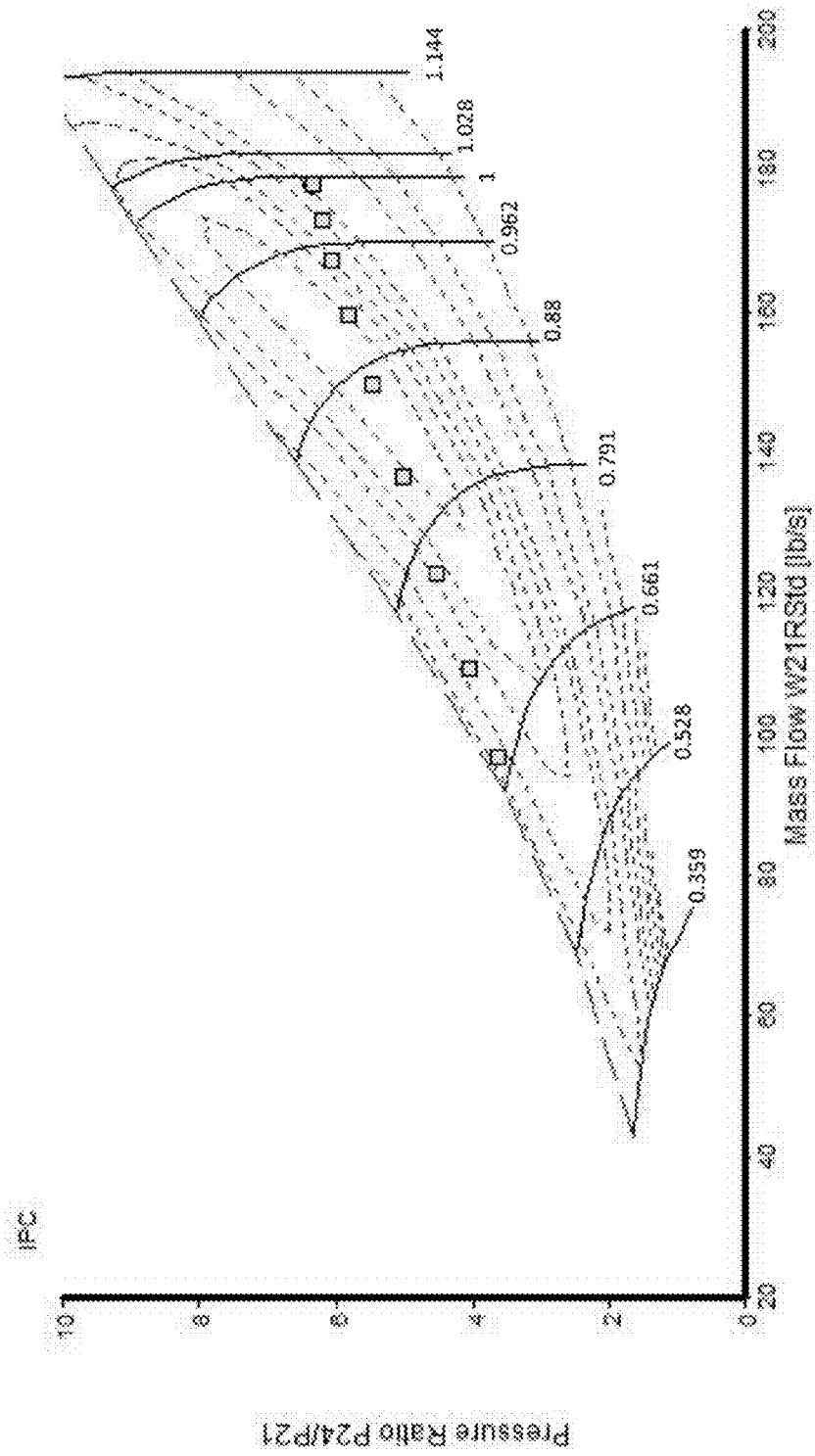
FIG. 9 is a graph of a typical compressor map for a low pressure compressor.

An example of this can be seen in the compressor map shown in FIG. 9. The map provided in FIG. 9 is a graph of a typical compressor map for a low pressure compressor. The vertical axis shows the pressure ratio through the compressor, and the horizontal axis is a measure of the mass of air flowing through the compressor. The upper-most dashed line is the surge line for the compressor, above which the compressor is unstable and will experience stall. The closer one can operate to the surge line, the greater the efficiency of the compressor becomes. Without any active monitoring of the onset of compressor stall, however, the margin of safety requires working at much lower efficiencies. The dotted contours represent the isentropic efficiency of the compressor. In order to ensure the engine does not experience compressor stall the engine is limited to operate along the line shown by squares the "working line"). As one can see, at higher speeds the working line rapidly drops off towards lower efficiencies, in order to ensure that the engine does not approach surge.

After detecting and recording the amount of light reflected by the blade and received by each of the receive optical fibers of the system, a computer algorithm determines the twist angle of the passing blade and stores the data in a computer-readable storage medium. In an embodiment, the algorithm then compares the twist angle data of the blade to the data from each of the preceding blades in the same revolution to determine if the twist angle of the blade in question in different from the twist angles of the preceding blades. If a difference greater than an acceptable range is detected, a signal is sent to a control algorithm to indicate that stall avoidance procedures should be initiated with respect to the compressor. If no difference is detected, the system continues to operate normally without sending a signal to the control system.

Figure 10:
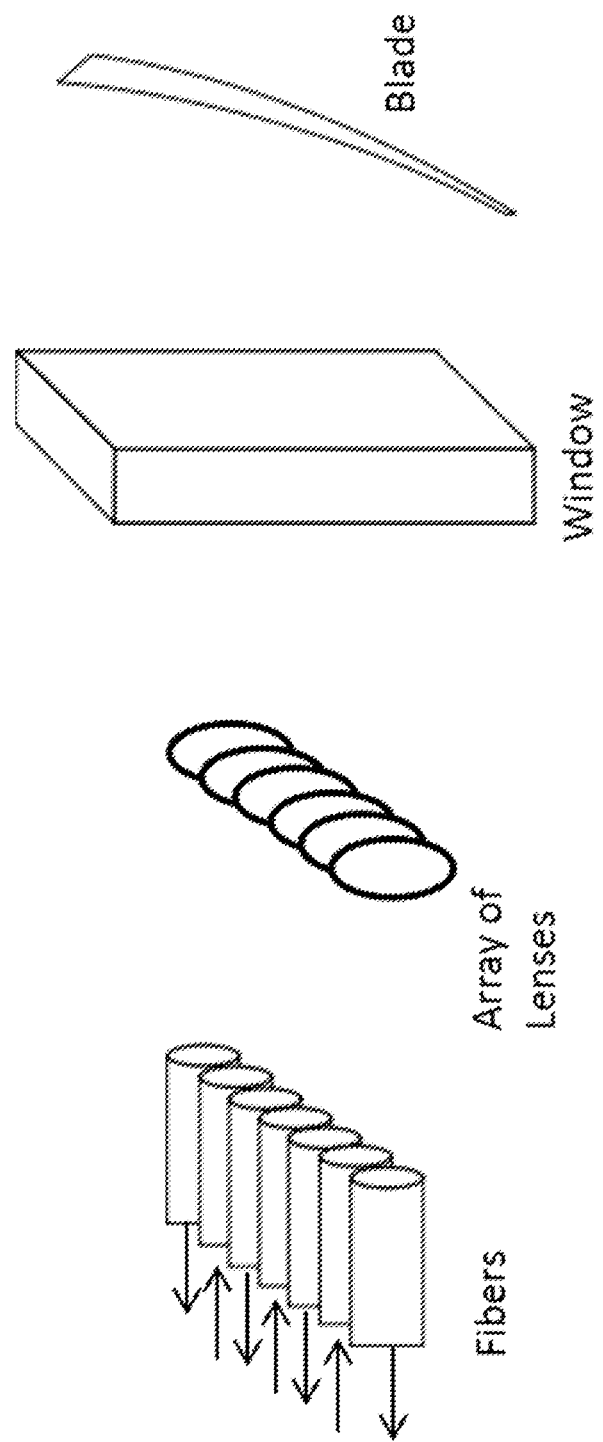
FIG. 10 is a schematic diagram showing a perspective view of an embodiment of a system of the invention comprising multiple light sources and an array of lenses.

FIG. 10 is a schematic diagram showing a perspective view of an embodiment of a system of the invention comprising multiple light sources and an array of lenses.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. It is intended that the specification and examples be considered as exemplary in nature and that variations that do not depart from the essence of the invention are intended to be within the scope of the invention. Further, the references cited in this disclosure are incorporated by reference herein in their entireties.

The invention claimed is:

1. A system for detecting the onset of stall in turbomachinery comprising:
    one or more optical sources operably configured for transmitting light toward one or more blades;
    one or more optical detectors operably configured for receiving light reflected from a plurality of points disposed widthwise across the one or more blades; and
    a processor in operable communication with the detector for determining blade twist angle and for measuring intensity of the reflected light to identify onset of stall; and
    a plurality of optical fibers linearly arranged in a row for transmitting light from the one or more optical sources and for transmitting light reflected from a blade to the one or more detectors.

2. The system of claim 1, wherein the light is visible light.

3. The system of claim 1, wherein the light is non-visible light.

4. A system for detecting the onset of stall in turbomachinery comprising:
    one or more optical sources operably configured for transmitting light toward one or more blades;
    one or more optical detectors operably configured for receiving light reflected from a plurality of points disposed widthwise across the one or more blades;
    a processor in operable communication with the detector for determining blade twist angle and for measuring intensity of the reflected light to identify onset of stall; and
    a plurality of optical fibers arranged in multiple rows for transmitting light from the one or more optical sources and for transmitting light reflected from a blade to the one or more detectors.

5. The system of claim 1 comprising a cylindrical lens to increase the light capture efficiency of the optical detectors.

6. The system of claim 1 comprising an array of lenses to increase the light capture efficiency of the optical detectors.

7. The system of claim 1 operably configured to steer a path of light from the one or more optical sources or to the one or more optical detectors to improve capture efficiency of the one or more optical detectors.

8. The system of claim 1, which is a system for detecting onset of compressor stall:
    wherein the one or more blades is one or more compressor blades; and
    wherein the processor is configured to measure intensity of the reflected light to determine blade twist angle and identify onset of compressor stall.

9. A computer program embodied in a computer-readable storage medium, which when executed, enables a computer to perform a method for detecting the onset of compressor stall, the method comprising:
    transmitting light from one or more optical fiber toward one or more blades of a compressor moving through the plane of light;
    receiving light reflected from the blade into a plurality of receive optical fibers, which are arranged linearly in a row;
    measuring intensity of the light reflected from the blade;
    calculating blade twist angle from the light intensity; and
    comparing the blade twist angle to a twist angle of one or more preceding blades to determine the onset of compressor stall.

10. The computer program of claim 9, wherein the method further comprises signaling a control system in operable communication with the compressor to initiate stall avoidance procedures.

11. A method for detecting the onset of compressor stall comprising:
    transmitting light from one or more optical fiber toward one or more blades of a compressor moving through the plane of light;
    receiving light reflected from the blade into a plurality of receive optical fibers, which are arranged linearly in a row;
    measuring intensity of the light reflected from the blade;
    calculating blade twist angle from the light intensity; and
    comparing the blade twist angle to a twist angle of one or more preceding blades to determine the onset of compressor stall.

12. The method of claim 11, further comprising signaling a control system in operable communication with the compressor to initiate stall avoidance procedures.

13. The method of claim 11, further comprising determining the onset of compressor stall with engine operational data.

14. The method of claim 11, wherein the engine operational data is one or more of rotational speed, pressure, or temperature.

15. The system of claim 4, wherein the light is visible light.

16. The system of claim 4, wherein the light is non-visible light.

17. The system of claim 4 comprising an array of lenses to increase the light capture efficiency of the optical detectors.

18. The system of claim 4 operably configured to steer a path of light from the one or more optical sources or to the one or more optical detectors to improve capture efficiency of the one or more optical detectors.

19. The system of claim 4, which is a system for detecting onset of compressor stall:
    wherein the one or more blades is one or more compressor blades; and wherein the processor is configured to measure intensity of the reflected light to determine blade twist angle and identify onset of compressor stall.

* * * * *